United States Patent
Kodera et al.

(10) Patent No.: US 8,454,978 B2
(45) Date of Patent: *Jun. 4, 2013

(54) IMMUNOSTIMULATING AGENT

(75) Inventors: Tomohiro Kodera, Kawasaki (JP); Yuzuru Eto, Kawasaki (JP); Yoshinori Mine, Shizuoka (JP)

(73) Assignee: Ajinomoto Co., Inc., Tokyo (JP)

( * ) Notice: Subject to any disclaimer, the term of this patent is extended or adjusted under 35 U.S.C. 154(b) by 195 days.

This patent is subject to a terminal disclaimer.

(21) Appl. No.: 12/899,045

(22) Filed: Oct. 6, 2010

(65) Prior Publication Data

US 2011/0070270 A1    Mar. 24, 2011

Related U.S. Application Data

(63) Continuation of application No. PCT/JP2009/057721, filed on Apr. 17, 2009.

(30) Foreign Application Priority Data

Apr. 17, 2008  (JP) .................................. 2008-108063

(51) Int. Cl.
 *A61K 38/05* (2006.01)
(52) U.S. Cl.
 USPC ......... 424/278.1; 514/2.3; 514/2.4; 514/17.4; 514/19.3; 514/21.91
(58) Field of Classification Search
 None
 See application file for complete search history.

(56) References Cited

U.S. PATENT DOCUMENTS

| | | | |
|---|---|---|---|
| 6,340,483 B1 * | 1/2002 | Goren et al. ................ | 424/754 |
| 7,670,822 B2 | 3/2010 | Smirnov et al. | |
| 8,106,020 B2 * | 1/2012 | Ohsu et al. ................. | 514/21.91 |
| 2004/0101576 A1 | 5/2004 | Yagi et al. | |
| 2009/0239310 A1 | 9/2009 | Ohsu et al. | |
| 2009/0239808 A1 | 9/2009 | Ohsu et al. | |
| 2009/0275092 A1 | 11/2009 | Kodera et al. | |
| 2010/0105864 A1 | 4/2010 | Yoneda et al. | |
| 2010/0120698 A1 | 5/2010 | Nagasaki et al. | |
| 2010/0136197 A1 | 6/2010 | Eto et al. | |
| 2010/0183792 A1 | 7/2010 | Nagasaki et al. | |

FOREIGN PATENT DOCUMENTS

| | | |
|---|---|---|
| JP | 11-292737 | 10/1999 |
| WO | WO98/30228 | 7/1998 |
| WO | WO98/42363 | 10/1998 |
| WO | WO00/54788 | 9/2000 |
| WO | WO2007/027548 | 3/2007 |
| WO | WO2007/055388 | 5/2007 |
| WO | WO2007/055393 | 5/2007 |
| WO | WO 2008139947 A1 * | 11/2008 |

OTHER PUBLICATIONS

U.S. Appl. No. 12/856,948 (Kodera et al), filed Aug. 16, 2010.*
U.S. Appl. No. 12/861,929 (Hara et al), filed Aug. 24, 2010.*
Supplementary European Search Report for European Patent App. No. 09733522.8 (Sep. 12, 2011).
International Search Report for PCT Patent App. No. PCT/JP2009/057721 (Jun. 23, 2010).
Awae, K., et al., "Kangengata Glutathione (GSH) no Chokan Men eki ni Taisuru Eikyo," The Japanese Society of Nutrition and Food Science Taikai Koen Yoshishu, Apr. 1, 2004, vol. 58, p. 116, 2E-10p, with an English translation.
Furukawa, T., "Tokushu.Roka to Saibo Fukatsu Saibo Fukatsu Busshitsu 'Glutathione' no Hataraki to sono Oyo," Fragrance Journal, 1987, vol. 15, No. 82, pp. 63-66, with a partial English translation.
Office Action from European Patent App. No. 09733522.8 (Feb. 7, 2013).

* cited by examiner

*Primary Examiner* — Jeffrey E Russel
(74) *Attorney, Agent, or Firm* — Shelly Guest Cermak; Cermak Nakajima LLP

(57) ABSTRACT

An immunostimulating agent, which can stimulate immunity effectively, is described. The immunostimulating agent contains an active ingredient including a calcium receptor activator such as γ-Glu-X-Gly [wherein X represents an amino acid or a derivative thereof other than Cys], γ-Glu-Val-Y [wherein Y represents an amino acid or a derivative thereof], γ-Glu-Ala, γ-Glu-Gly, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, γ-Glu-Met(O), γ-Glu-γ-Glu-Val, γ-Glu-Val-NH2, γ-Glu-Val-ol, γ-Glu-Ser, γ-Glu-Tau, γ-Glu-Cys(S-Me)(O), γ-Glu-Leu, γ-Glu-Ile, γ-Glu-t-Leu, γ-Glu-Cys(S-Me), a cation having a valency of 2 or more, protamine, polylysine, spermine, spermidine, putrescine, cinacalcet, a cinacalcet analogue compound, and a salt of any one of the aforementioned components.

6 Claims, No Drawings

IMMUNOSTIMULATING AGENT

This application is a continuation under 35 U.S.C. §120 of PCT Patent Application No. PCT/JP2009/057721, filed Apr. 17, 2009, which claims priority under 35 U.S.C. §119 to Japanese Patent Application No. 2008-108063, filed on Apr. 17, 2008, which are incorporated in their entireties by reference.

BACKGROUND OF THE INVENTION

1. Field of the Invention

The present invention relates to an immunostimulating agent that can be utilized in the fields of pharmaceuticals, foods, and the like.

2. Brief Description of the Related Art

Compounds such as glutathione, cinacalcet, and γ-glutamylvaline, as well as derivatives thereof, or analogs thereof, have an action of activating a calcium sensing receptor (CaSR) and it has been implied that these CaSR agonists can be used as therapeutic agents for internal diseases (WO2007/055388).

Also, an influenza virus infection prophylactic composition containing glutathione has been known (WO98/30228).

However, it has been unknown whether the CaSR agonist can significantly stimulate immunity.

SUMMARY OF THE INVENTION

An aspect of the present invention is to provide an immunostimulating agent capable of effectively stimulating immunity, as well as to provide foods and beverages containing said agent.

Calcium receptor activators, such as cinacalcet and γ-glutamylvaline, have an immunostimulating action and are described.

It is an aspect of the present invention to provide an immunostimulating agent containing a calcium receptor activator.

It is a further aspect of the present invention to provide the above-described immunostimulating agent, wherein the calcium receptor activator is selected from the group consisting of γ-Glu-X-Gly, γ-Glu-Val-Y, γ-Glu-Ala, γ-Glu-Gly, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, γ-Glu-Met(O), γ-Glu-γ-Glu-Val, γ-Glu-Val-NH$_2$, γ-Glu-Val-ol, γ-Glu-Ser, γ-Glu-Tau, γ-Glu-Cys(S-Me)(O), γ-Glu-Leu, γ-Glu-Ile, γ-Glu-t-Leu, γ-Glu-Cys(S-Me), a cation having a valence of two or more, protamine, polylysine, spermine, spermidine, putrescine, cinacalcet, cinacalcet analogous compounds, and salts thereof; wherein X is an amino acid or an amino acid derivative other than Cys; and wherein Y is an amino acid or an amino acid derivative.

It is a further aspect of the present invention to provide the above-described immunostimulating agent, wherein the X is Cys(SNO), Cys(S-allyl), Gly, Cys(S-Me), Abu, or Ser; and the Y is Gly, Val, Glu, Lys, Phe, Ser, Pro, Arg, Asp, Met, Thr, His, Orn, Asn, Cys, or Gln.

It is a further aspect of the present invention to provide the above-described immunostimulating agent, wherein the above-mentioned calcium receptor activator is γ-Glu-Val or cinacalcet.

It is a further aspect of the present invention to provide the above-described immunostimulating agent, which is used as a pharmaceutical for the treatment or prophylaxis of an infection, diarrhea, polyp, tumor, enteritis, or an allergy.

It is a further aspect of the present invention to provide a food or beverage for immunostimulation containing γ-Glu-Val or cinacalcet in an amount of 0.000000001% by mass or more.

It is a further aspect of the present invention to provide a method of manufacturing a calcium receptor activator comprising formulating a composition comprising an immunostimulating agent.

It is a further aspect of the present invention to provide the above-described use, wherein the calcium receptor activator is selected from the group consisting of γ-Glu-X-Gly, γ-Glu-Val-Y, γ-Glu-Ala, γ-Glu-Gly, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, γ-Glu-Met(O), γ-Glu-γ-Glu-Val, γ-Glu-Val-NH$_2$, γ-Glu-Val-ol, γ-Glu-Ser, γ-Glu-Tau, γ-Glu-Cys(S-Me)(O), γ-Glu-Leu, γ-Glu-Ile, γ-Glu-t-Leu, γ-Glu-Cys(S-Me), a cation having a valence of two or more, protamine, polylysine, spermine, spermidine, putrescine, cinacalcet, cinacalcet analogous compounds, and salts thereof; wherein X is an amino acid or an amino acid derivative other than Cys; wherein Y is an amino acid or an amino acid derivative.

It is a further aspect of the present invention to provide the above-described method, wherein the X is Cys(SNO), Cys(S-allyl), Gly, Cys(S-Me), Abu, or Ser; and the Y is Gly, Val, Glu, Lys, Phe, Ser, Pro, Arg, Asp, Met, Thr, His, Orn, Asn, Cys, or Gln.

It is a further aspect of the present invention to provide the above-described method, wherein the above-mentioned calcium receptor activator is γ-Glu-Val or cinacalcet.

It is a further aspect of the present invention to provide the above-described method of the calcium receptor activator for manufacturing a pharmaceutical for the treatment or prophylaxis of an infection, diarrhea, polyp, tumor, enteritis, or allergy.

It is a further aspect of the present invention to provide a method for stimulating immunity comprising administrating a calcium receptor activator to a subject in need of stimulation of immunity.

It is a further aspect of the present invention to provide the above-described method for stimulating immunity, wherein the calcium receptor activator is selected from the group consisting of γ-Glu-X-Gly, γ-Glu-Val-Y, γ-Glu-Ala, γ-Glu-Gly, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, γ-Glu-Met(O), γ-Glu-γ-Glu-Val, γ-Glu-Val-ol, γ-Glu-Ser, γ-Glu-Tau, γ-Glu-Cys(S-Me)(O), γ-Glu-Leu, γ-Glu-Ile, γ-Glu-t-Leu, γ-Glu-Cys(S-Me), a cation having a valence of two or more, protamine, polylysine, spermine, spermidine, putrescine, cinacalcet, cinacalcet analogous compounds, and salts thereof; wherein X represents an amino acid or an amino acid derivative other than Cys; and Y represents an amino acid or an amino acid derivative.

It is a further aspect of the present invention to provide the above-described method for stimulating immunity, wherein the X is selected from the group consisting of Cys(SNO), Cys(S-allyl), Gly, Cys(S-Me), Abu, or Ser; and the Y is Gly, Val, Glu, Lys, Phe, Ser, Pro, Arg, Asp, Met, Thr, His, Orn, Asn, Cys, and Gln.

It is a further aspect of the present invention to provide the above-described method for stimulating immunity, wherein the above-described calcium receptor activator is γ-Glu-Val or cinacalcet.

It is a further aspect of the present invention to provide a method for treating or preventing an infection, diarrhea, polyp, tumor, enteritis or an allergy, the method comprising administrating the above-described calcium receptor activator to a patient suffering from infection, diarrhea, polyp, tumor, enteritis, or an allergy.

DESCRIPTION OF THE PREFERRED EMBODIMENTS

An immunostimulating agent in accordance with the presently described subject matter contains a calcium receptor activator as an active ingredient.

The calcium receptor activator can be a peptide or low molecular weight compound having an action of activating a calcium receptor.

<1> Calcium Receptor Activator

The term "calcium receptor" can refer to a receptor that is known as Calcium Sensing Receptor (CaSR) and belongs to the class C of seven-transmembrane receptors. The term "calcium receptor activator" (hereinafter, also referred to as "CaSR activator") can include a substance that regulates the functions of CaSR-expressing cells by binding and activating the CaSR (hereinafter, also referred to as "CaSR agonist"), and a substance that functions to extend the CaSR activity by binding and activating the CaSR (hereinafter, also referred to as "CaSR modulator"). Furthermore, the term "CaSR activation" can mean that a ligand binds to a calcium receptor to activate a guanine nucleotide binding protein, and thereby transduces a signal. In addition, transduction of this signal by the calcium receptor can be referred to as "CaSR activity".

A CaSR activator can be obtained by a screening method described below, for example, but the methods are not limited to them. The CaSR activator and screening method thereof are also described in WO2007/055388 in detail.

A CaSR agonist and modulator can be obtained via screening by determining the presence or absence of CaSR activation by a test substance using CaSR-expressing cells.

The presence or absence of CaSR activation can be examined by measuring the amount of a substance (ligand) that binds to CaSR, a substance that inhibits a reaction with a signal for regulating the CaSR activity, a substance (such as a second messenger) that transduces a signal generated by the binding of a ligand to the CaSR, or the like. For example, CaSR activation can be measured by detecting a second messenger generated by the binding of a ligand such as $Ca^{2+}$ to CaSR. Furthermore, CaSR activation can also be measured by using a radio-labeled, known ligand, and measuring the binding of the radio-labeled ligand to the CaSR.

The CaSR bound to a ligand can act on a GTP binding protein (also referred to as a G protein, such as Gi or Gq) to control various cell functions via a second messenger such as cAMP. In particular, Gq activation increases the intracellular calcium concentration. Furthermore, downstream of the increase in intracellular calcium concentration in the signal transduction pathway, functions are acutely regulated through the activation of intracellular enzymes such as calmodulin, protein kinase C, and adenylate cyclase, and through the phosphorylation of cytoplasmic proteins/cell membrane proteins. The activation of intracellular enzymes can alter channel function in the cell membrane. Thus, the presence or absence of CaSR activation by a test substance can be detected by bringing the test substance into contact with CaSR-expressing cells, and observing G protein activation using a pre-determined intracellular calcium concentration, the amount of intracellular cAMP, the channel function (such as the extracellular proton production amount), or the like, as an indicator.

CaSR-expressing cells that can be used for screening can be, for example, cells derived from animals including mammals such as mice, rats, hamsters, guinea pigs, rabbits, dogs, monkeys, and human beings, and avian species such as chickens. Furthermore, the origin of the CaSR is not particularly limited, and, for example, can be a CaSR derived from the above-described animals. Specifically, the human CaSR encoded by the human CaSR gene registered under GenBank Accession No. NM_000388 can be used. It should be noted that the CaSR is not limited to the protein encoded by the gene having the above-described sequence, and can be a protein encoded by a gene having a homology of 60% or more, or in other examples 80% or more, 90% or more, and 98% or more, to the above-described sequence as long as the gene encodes a protein having the CaSR function. The GPRC6A receptor or 5.24 receptor is also known as a subtype of the CaSR, and can be used.

The test substance that can be used in screening can be a known or novel compound, and examples include nucleic acids, saccharides, lipids, proteins, peptides, organic low-molecular weight compounds, compound libraries prepared by using combinatorial chemistry techniques, random peptide libraries prepared by solid phase synthesis or a phage display method, and natural ingredients derived from microorganisms, animals and plants, marine organisms, or the like.

A first screening method (hereinafter, also referred to as "method A") can include, for example, the following steps (a), (b), and (c):

(a) a step of bringing CaSR-expressing cells into contact with a test substance;

(b) a step of measuring the G protein activation in the cells brought into contact with the test substance, and comparing such activation with the activation in control cells not brought into contact with the test substance; and (c) a step of selecting a substance capable of activating CaSR based on the comparison results in step (b).

In step (a), the CaSR-expressing cells are kept in contact with the test substance, which can occur in a culture medium. The culture medium is appropriately selected depending on the type of cells to be used and the like.

In step (b), firstly, the activation of G proteins in the CaSR-expressing cells in the presence of the test substance can be evaluated. Next, this activation is compared with the activation in the absence of the test substance. Here, examples of an indicator, which can be used to measure the activation of G proteins, include the intracellular calcium concentration, the amount of intracellular cAMP, the amount of extracellular protein, and the like.

In step (c), the comparison of the activations can be conducted based on, for example, the presence or absence of a significant difference. As a result of the evaluation, if the activation is increased or extended in the presence of the test substance as compared to that in the absence of the test substance, the test substance can be assessed as a CaSR agonist.

Also, when screening for a CaSR modulator in step (a), the test substance and a CaSR agonist can be brought into contact with the CaSR-expressing cells; in step (b), the activation of G proteins when the CaSR agonist was brought into contact with the cells in the presence of the test substance is compared with the activation of G proteins when the CaSR agonist is brought into contact with the cells in the absence of the test substance; and in step (c), a substance which extends the activation of G proteins can be selected as a CaSR modulator.

A second screening method for a CaSR agonist or modulator can include, for example, the following steps (a), (b), and (c):

(a) a step of bringing a test substance and a ligand acting on CaSR into contact with CaSR-expressing cells;

(b) a step of measuring the amount of the ligand bound to the cell membrane of the cells, and comparing the amount of the ligand with the amount of the ligand in control cells not brought into contact with the test substance; and (c) a step of selecting a substance capable of activating CaSR based on the comparison results in step (b).

In step (a) of the second screening method, the CaSR-expressing cells are kept in contact with the test substance and the ligand acting on CaSR. The contact of the test substance and the ligand acting on CaSR, which can occur in a culture medium. The culture medium can be appropriately selected depending on the kind of cells to be used and the like.

In step (b), firstly, the amount of the ligand bound to the cell membrane of the CaSR-expressing cells in the presence of the test substance can be evaluated. Next, the amount of the ligand is compared with the amount of the ligand in the absence of the test substance. The amount of the ligand bound can be measured, for example, by using a radio-labeled ligand or the like.

In step (c), the comparison of the amounts of the ligand is conducted based on, for example, the presence or absence of a significant difference. As a result of the evaluation, if the amount of the ligand bound is decreased in the presence of the test substance as compared to that in the absence of the test substance, the test substance can be assessed as a CaSR agonist or a CaSR modulator.

In addition, substances that cause a decrease in the amount of bound ligand as determined by screening method A, can be confirmed as CaSR agonists.

The ligand acting on CaSR is not particularly limited, and examples include $Ca^{2+}$, cinacalcet, and the like.

Hereinafter, specific methods (1) to (3) for detecting an immunostimulating substance using CaSR-expressing cells (cells having a functional CaSR) are exemplified.

(1) A method including the following steps (a), (b), and (c):

(a) a step of bringing CaSR-expressing cells into contact with a test substance for a certain period of time;

(b) a step of measuring the cAMP amount in the cells brought into contact with the test substance, and comparing the cAMP amount with the cAMP amount in control cells not brought into contact with the test substance; and (c) a step of selecting a substance capable of activating CaSR based on the comparison results of step (b).

The cAMP amount can be measured with a commercially available assay kit.

In step (a) of the above-described screening method, when screening for a CaSR modulator, the test substance and a CaSR agonist can be brought into contact with the CaSR-expressing cells.

In step (b) of the above-described screening method, when screening for a CaSR modulator, the amount of cAMP produced when a CaSR agonist is brought into contact with the cells in the presence of the test substance can be compared with the amount of cAMP when the CaSR agonist into contact with the cells in the absence of the test substance.

In step (c) of the above-described screening method, the cAMP amounts can be compared based on, for example, the presence or absence of a significant difference. As a result of the evaluation of the cAMP amount, if it can be confirmed that the cAMP amount increases, the test substance can be assessed as a substance capable of activating CaSR. When screening for a CaSR modulator, a large increase in the cAMP amount indicates that the substance is a CaSR modulator.

(2) A method comprising the following steps (a), (b), and (c):

(a) a step of bringing a test substance and a known ligand (such as $Ca^{2+}$ or cinacalcet) acting on CaSR into contact with CaSR-expressing cells for a certain period of time;

(b) a step of measuring the amount of the ligand bound to the cell membrane of the cells, and comparing this amount of the ligand with the amount of the ligand in control cells not brought into contact with the test substance; and (c) a step of selecting a substance capable of activating CaSR based on the comparison results in the above-described step (b).

The amount of the known ligand can be measured by radio-labeling a part of the substances, and determining the amount of radioactivity bound to the cell membrane.

In step (c) of the above-described screening method, the amounts of the ligand can be Compared based on, for example, the presence or absence of a significant difference. As a result of the evaluation of the amount of the ligand, if it can be confirmed that the amount of the ligand bound decreases, the test substance can be assessed as a CaSR agonist or modulator.

(3) A method containing the following steps (a), (b), and (c):

(a) a step of bringing CaSR-expressing cells containing a cAMP-sensitive fluorescent protein (such as FlCRhR) into contact with a test substance for a certain period of time;

(b) a step of measuring the fluorescence intensity (intracellular cAMP concentration) in the cells brought into contact with the test substance, and comparing this intensity with the intensity in control cells not brought into contact with the test substance; and (c) a step of selecting a substance capable of activating CaSR based on the comparison results in the above-described step (b).

In step (a) of the above-described screening method, when screening for a CaSR modulator, the test substance and a CaSR agonist can be brought into contact with the CaSR-expressing cells containing a cAMP-sensitive fluorescent protein (such as FlCRhR).

In step (b) of the above-described screening method, when screening for a CaSR modulator, the fluorescence intensity (intracellular cAMP concentration) when a CaSR agonist is brought into contact with the cells in the presence of the test substance can be compared with the fluorescence intensity (intracellular cAMP concentration) when the CaSR agonist is brought into contact with the cells in the absence of the test substance.

In step (c) of the above-described screening method, the fluorescence intensities can be compared based on, for example, the presence or absence of a significant difference. As a result of the evaluation of the fluorescence intensity, if it can be confirmed that the fluorescence intensity increases, the test substance can be assessed as a CaSR agonist. When screening for a CaSR modulator, a large increase in the fluorescence intensity can indicate that the substance is a CaSR modulator.

The CaSR activator (CaSR agonist or modulator) obtained as above can be confirmed to have an immunostimulating activity. The immunostimulating activity can be confirmed, for example, by a method using as an indicator an action of promoting the production of IgA or IgG, such as those described in the Examples, or cytokines such as IL-6 or IFN-γ, which are able to modulate antibody production.

Specific examples of the CaSR agonist include various peptides such as γ-Glu-X-Gly (X represents an amino acid or an amino acid derivative other than Cys), γ-Glu-Val-Y (Y represents an amino acid or an amino acid derivative), γ-Glu-Ala, γ-Glu-Gly, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, γ-Glu-Met(O), γ-Glu-γ-Glu-Val, γ-Glu-Val-NH₂, γ-Glu-Val-ol, γ-Glu-Ser, γ-Glu-Tau, γ-Glu-Cys(S-Me)(O), γ-Glu-Leu, γ-Glu-t-Leu, and γ-Glu-Cys(S-Me); amino acids such as phenylalanine and tryptophan; cations having a valence of two or more such as calcium and gadolinium; proteins such as protamine; basic peptides such as polylysine; polyamines such as spermine, spermidine or putrescine; and various low molecular weight compounds such as cinacalcet and cinacalcet analogous compounds.

It should be noted that each of the amino acids which constitute a peptide is in the L-form unless otherwise stated. Herein, examples of the amino acids include: a neutral amino acid such as Gly, Ala, Val, Leu, Ile, Ser, Thr, Cys, Met, Asn, Gln, Pro, or Hyp; an acidic amino acid such as Asp or Glu; a basic amino acid such as Lys, Arg, or His; an aromatic amino acid such as Phe, Tyr, or Trp; and homoserine, citrulline, ornithine, α-aminobutyric acid, norvaline, norleucine, and taurine.

In the present description, abbreviations for amino acid residues mean the following amino acids:
(1) Gly: Glycine
(2) Ala: Alanine
(3) Val: Valine
(4) Leu: Leucine
(5) Ile: Isoleucine
(6) Met: Methionine
(7) Phe: Phenylalanine
(8) Tyr: Tyrosine
(9) Trp: Tryptophan
(10) His: Histidine
(11) Lys: Lysine
(12) Arg: Arginine
(13) Ser: Serine
(14) Thr: Threonine
(15) Asp: Aspartic acid
(16) Glu: Glutamic acid
(17) Asn: Asparagine
(18) Gln: Glutamine
(19) Cys: Cysteine
(20) Pro: Proline
(21) Orn: Ornithine
(22) Sar: Sarcosine
(23) Cit: Citrulline
(24) N-Val: Norvaline
(25) N-Leu: Norleucine
(26) Abu: α-Aminobutyric acid
(27) Tau: Taurine
(28) Hyp: Hydroxyproline
(29) t-Leu: tert-Leucine Furthermore, the amino acid derivative can represent various derivatives of the above-described amino acids, and examples include an unusual amino acid, a non-natural amino acid, an amino alcohol, or an amino acid in which an amino acid side chain, such as the terminal carbonyl group, the terminal amino group, or the thiol group of cysteine, is replaced with various substituents. Examples of the substituents include an alkyl group, an acyl group, a hydroxyl group, an amino group, an alkylamino group, a nitro group, a sulfonyl group, and various protection groups. Examples of the substituted amino acid include: Arg(NO₂): N-γ-nitroarginine, Cys(SNO): S-nitrocysteine, Cys(S-Me): S-methylcysteine, Cys(S-allyl): S-allylcysteine, Val-NH₂: valinamide, and Val-ol: valinol (2-amino-3-methyl-1-butanol).

It should be noted that the "(O)" in γ-Glu-Met(0) and γ-Glu-Cys(S-Me)(O) indicates a sulfoxide structure. The "γ:gamma" in γ-Glu indicates that the glutamic acid binds to another amino acid via the carboxy group at the γ position of the glutamic acid.

In the peptide, "X" can be Cys(SNO), Cys(S-allyl), Gly, Cys(S-Me), Abu, or Ser, and "Y" can be Gly, Val, Glu, Lys, Phe, Ser, Pro, Arg, Asp, Met, Thr, His, Orn, Asn, Cys, or Gln. However, "X" and "Y" are not limited thereto. Another example of the peptide is γ-Glu-Val-Gly.

A commercially available product can be used as the above-described peptide. Furthermore, the peptide can be obtained by appropriately employing a known technique such as (1) a chemical synthesis method, or (2) a synthesis method through an enzymatic reaction. The peptide can contain 2 to 3 amino acid residues, that is, it is relatively short, and hence, the chemical synthesis method is convenient. In the case of the chemical synthesis, the oligopeptide can be synthesized or semi-synthesized by using a peptide synthesizer. An example of the chemical synthesis method is a peptide solid phase synthesis method. The peptide synthesized as described above can be purified by general means such as ion exchange chromatography, reversed-phase high performance liquid chromatography, or affinity chromatography. Such a peptide solid phase synthesis method and the subsequent peptide purification are well known in the technical field.

Furthermore, the peptide can also be produced by an enzymatic reaction. For example, the method described in WO 2004/011653 A1 can be employed. That is, the peptide can also be produced by reacting one amino acid or dipeptide with an esterified or amidated carboxyl terminus with an amino acid having a free amino group (for example, an amino acid whose carboxyl group is protected) in the presence of a peptide-producing enzyme, and purifying the produced dipeptide or tripeptide. The peptide-producing enzyme can be a part of a composition which includes a culture of a microorganism having an ability to produce the peptide, microbial cells which have been separated from such a culture, and a processed product of these microbial cells. The peptide-producing enzyme can also be purified or derived from the microorganism that produces it.

It should be noted that the peptide can not only be produced by such enzymatic chemical synthesis methods, but also can be derived from, for example, a plant such as a vegetable or a fruit, a microorganism such as a yeast, and a yeast extract. When the peptide is native to a natural product, the peptide can be extracted from the product.

Furthermore, the peptide does not need to be isolated before use, and a fraction containing the peptide in a large amount can also be used.

Examples of the low molecular weight compound include cinacalcet ((R)—N-(3-(3-(trifluoromethyl)phenyl)propyl)-1-(1-naphthyl)ethylamine), and analogous compounds thereof. Examples of the analogous compounds of cinacalcet include the compound represented by the following chemical formula (1): ((R)—N-[(4-ethoxy-3-methylphenyl)methyl]-1-(1-naphthyl)ethylamine)), and the compound represented by the following chemical formula (2): ((R)—N-(3-phenyl-prop-2-enyl)-1-(3-methoxyphenyl)ethylamine). These compounds can be synthesized, for example, by a known method, such as that described in U.S. Pat. No. 6,211,244. Furthermore, a commercially available product can also be used.

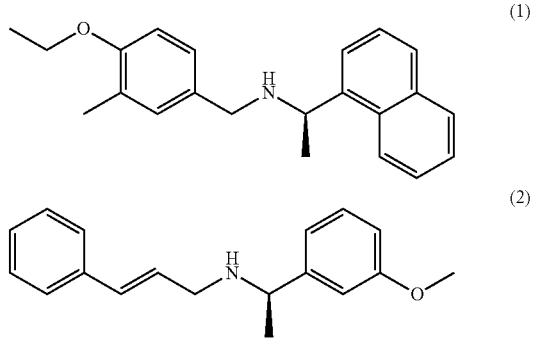

In addition, examples of CaSR activators include a compounds described in U.S. Pat. No. 6,211,244, WO06/123725, WO05/115975, U.S. Pat. Nos. 6,313,146, 6,213,146, 5,688,938, 5,763,569, 5,858,684, 5,962,314, 6,001,884, 6,011,068, and 6,031,003, WO 95/11221, WO 1996/012697, WO 2002/059102 or JP 1999-130737.

A part of or all of the CaSR activator can also be used in the form of a salt as well as a free compound. Therefore, the term "CaSR activator" can include both the free compound and a salt thereof. Examples of the salt form which include acid addition salts and salts with a base, and a salt which is acceptable for use in a pharmaceutical or a food, can be used. Such salt forms include, for example, an inorganic salt such as a hydrochloride, a hydrobromide, a sulfate, or a phosphate, or an organic salt such as an acetate, a lactate, a citrate, a tartrate, a maleate, a fumarate, or a monomethyl sulfate.

<2> Immuno Stimulating Agent

The immunostimulating agent contains a CaSR activator as an active ingredient. Examples of the immunostimulating agent include, but are not limited to, pharmaceuticals, quasi-drugs, foods and beverages.

Examples of an immune system stimulated by the immunostimulating agent include, but are not limited to, mucosal tissues such as the intestinal tract, oral cavity, nose, and respiratory organs, and the spleen. By stimulating these immune systems, immunities are improved. Thus, the immunostimulating agent can be effective for the treatment or prophylaxis of diseases such as various infections, diarrhea, polyps, tumors, enteritis, or allergies.

The infections include viral infections and bacterial infections. The viral infections are not particularly limited, and examples include gastrointestinal viral infections (for example, enterovirus and cytomegalovirus), respiratory viral infections (infections caused by respiratory viruses such as influenza virus, rhinovirus, coronavirus, parainfluenza virus, RS virus, adenovirus, and reovirus), herpes zoster caused by herpesvirus, diarrhea caused by rotavirus, viral hepatitis, and AIDS. The immunostimulating agent can be particularly effective for the gastrointestinal viral infections.

Furthermore, the bacterial infections are not particularly limited, and examples include infections caused by *Bacillus cereus, Vibrio parahaemolyticus*, enterohemorrhagic *Escherichia coli, Staphylococcus aureus*, MRSA, *Salmonella, Clostridium botulinum*, and *Candida*.

The term "immunostimulation" can refer to the activation of an organism's intrinsic immune system. Specifically, for example, it can mean the promotion of the secretion of IgA and/or IgG in immune organs or immune tissues, including mucosal tissues of the intestinal tract such as the small intestine; mucosal tissues such as oral cavity, nose, and respiratory organs; and the spleen.

Depression of the immune system can lead to the development of diseases of the intestinal tract, including, but not limited to, infections, allergy diseases, polyps, tumors, and enteritis (Lecture on intestinal immune system, www.ioudou.co.jp/col/archives/2004/11/post_7.html).

A CaSR activator has an action of promoting the secretion of IgA or IgG. For example, secretory IgA specifically binds to microorganisms such as invasive bacteria or viruses, and prevents the adhesion of these microorganisms to epithelial cells. Furthermore, secretory IgA can neutralize toxins produced by bacteria such as *Vibrio cholerae*, and prevents the absorption of food antigens into a body by binding to allergens contained in foods (Hisako Yasui, Intestinal immune system-regulating action of *bifidobacterium*, www.healthist.jp/special/150_03/03_03.html).

In addition, secretory IgA is involved in the induction of "oral immune tolerance" which is an immunosuppressing mechanism for proteins absorbed from the intestinal tracts (Satoshi Hachimura, Intestinal immune system as contact between food and immune system: Its unique cell responsiveness, jsbba.bt.a.u-tokyo.ac.jp/03reikai3/hachimura.pdf). Thus, allergies can be suppressed by inducing the oral immune tolerance.

Accordingly, it is believed that stimulating the immune system, for example, by promoting the secretion of IgA in the intestinal tracts, is effective for the treatment or prophylaxis of the above-described diseases.

Methods for administering the immunostimulating agent are not particularly limited and examples include, but are not limited to, oral administration, invasive administration such as injection, suppository administration, and transdermal administration. The active ingredient can be combined with a solid or liquid non-toxic carrier for pharmaceuticals. The carrier can be suitable for administration methods such as oral administration and injection, to administer the active ingredient in the form of a conventional pharmaceutical formulation. Examples of such a formulation include solid drugs such as tablets, granules, powders, or capsules; liquid drugs such as solutions, suspensions, or emulsions; and freeze dried drugs. These formulations can be prepared by a conventional method or various pharmaceutical formulation forms to be developed in the future.

Examples of the above-described non-toxic carrier for pharmaceuticals include, but are not limited to, glucose, lactose, sucrose, starch, mannitol, dextrin, fatty acid glyceride, polyethylene glycol, hydroxyethylated starch, ethylene glycol, polyoxyethylene sorbitan fatty acid ester, gelatin, albumin, amino acid, water, physiological saline. Furthermore, if necessary, a commonly used additive such as a stabilizer, a humectant, an emulsifier, a binder, or a tonicity agent can also be added.

The immunostimulating agent can contain, in addition to the CaSR activator, one kind or two or more kinds of other drugs having an immunostimulating action, and that are effective for the treatment or prevention of a target disease such as infections. Examples of such a drug include, but are not limited to, cystine or a derivative thereof, theanine, and lactic acid bacteria.

The dosage or intake of the immunostimulating agent can be any amount as long as it is effective for the treatment and/or prophylaxis. Accordingly, the dosage can be appropriately adjusted depending on the patient's age, gender, body weight, and symptoms. For example, in the case of oral administration, the dosage can be 0.0000001 to 10 g/kg body weight per day for an adult, in terms of the amount of the CaSR activator, or 0.000001 to 1 g/kg body weight. The number of administrations is not particularly limited and the administration can be carried out once to several times per day.

The content of the CaSR activator in the immunostimulating agent is not limited as long as it is effective for the above-described dosage. The content of the CaSR activator can be, for example, 0.000001% by mass to 99.9999% by mass per dry weight, or in other examples, 0.00001% by mass to 99.999% by mass, and 0.0001% by mass to 99.99% by mass.

The immunostimulating agent containing a CaSR activator can be incorporated into a food or beverage. The form of the food or beverage is not particularly limited, and examples include, but are not limited to, seasonings, fermented foods, alcoholic beverages, soups, sauces, mayonnaise, dressings, curry roux, juices, nutritional drinks, rice gruel, bread, confectioneries, retort pouch foods, frozen foods, supplements, and oral cosmetics.

The food or beverage can be manufactured by the same method using the same raw materials by which it is normally manufactured, except that the CaSR activator is blended into it. Such raw materials are not particularly limited, and examples include, but are not limited to, rice, barley, and corn starch for alcohol beverages; wheat flour, sugar, salt, butter, and yeast for fermentation, for bread; and soy beans and wheat for fermented foods.

The food or beverage can contain the CaSR activator in an amount of, for example, 0.000000001% by mass or more, or in other examples, 0.000001% by mass or more, and 1% by mass or more.

Foods and beverages described above can have an immunostimulating effect and can be marketed and sold with health claims, which means the food and beverage packaging can include a label indicating that the food or beverage has such an immunostimulating effect, a therapeutic effect, or a prophylactic effect against the above-described diseases.

EXAMPLES

Hereinafter, the present invention is more specifically described by way of examples. However, the present invention is not limited thereto. Please note that cinacalcet was synthesized by the method described in the following Production Example 1.

Production Example 1

Synthesis of (R)—N-(3-(3-trifluoromethylphenyl) propyl)-1-(1-naphthyl)ethylamine hydrochloride (Cinacalcet hydrochloride)

Step 1: Synthesis of 3-(3-trifluoromethylphenyl)-propionic acid methyl ester

A mixture of 2.20 g of 3-(trifluoromethyl) cinnamic acid, 166 mg of palladium/carbon (10%, wet), and 40 ml of ethanol was stirred overnight under a hydrogen atmosphere at 1 atm. Palladium/carbon was separated by filtration, and the filtrate was concentrated under reduced pressure. 20 ml of methanol and 4 drops of concentrated sulfuric acid were added and the mixture was stirred at 60° C. for 2 hours, and then left to cool down. After concentration under reduced pressure, 20 ml of a saturated sodium bicarbonate aqueous solution was added, and the resultant was extracted with 20 ml of dichloromethane. The extract was dried with anhydrous sodium sulfate and then concentrated under reduced pressure to afford 2.40 g of the captioned compound as an oil.

$^1$H-NMR (300 MHz, CDCl$_3$) δ 2.66 (2H, t, J=7.5 Hz), 3.02 (2H, t, J=7.5 Hz), 3.68 (3H, s), 7.37-7.50 (4H, m)

Step 2: Synthesis of 3-(3-trifluoromethylphenyl)propanal 2.40 g of 3-(3-trifluoromethylphenyl)-propionic acid methyl ester synthesized in Step 1 was dissolved in 20 ml of dry dichloromethane. 13 ml of diisopropyl aluminum hydride solution (0.91 M) in hexane was dropped over 5 minutes at −78° C. under an argon atmosphere, and the mixture was stirred at the same temperature for 40 minutes. 50 ml of a saturated ammonium chloride aqueous solution was dropped, and then the mixture was stirred and the temperature was raised to room temperature. 20 ml of water and 5 ml of concentrated hydrochloric acid were added, and the resultant was separated into an aqueous layer and an organic layer. The aqueous layer was extracted with dichloromethane, and the extract was combined with the separated organic layer, dried over anhydrous sodium sulfate, and then concentrated under reduced pressure to afford 2.12 g of the captioned compound as an oil.

$^1$H-NMR (300 MHz, CDCl$_3$) δ 2.83 (2H, t-t, J=7.5 Hz, 1.2 Hz), 3.02 (2H, t, J=7.5 Hz), 7.36-7.52 (4H, m), 9.83 (1H, t, J=1.2 Hz)

Step 3: Synthesis of (R)—N-(3-(3-trifluoromethylphenyl)propyl)-1-(1-naphthyl) ethylamine hydrochloride (Cinacalcet hydrochloride)

To a mixture of 2.12 g of 3-(3-trifluoromethylphenyl)propanal synthesized in the Step 2, 2.0 ml of (R)-1-(1-naphthyl) ethylamine, 3.42 g of sodium triacetoxyborohydride, and 150 ml of dry dichloromethane was added 0.750 ml of glacial acetic acid, and the mixture was stirred at room temperature for 5 hours. After 100 ml of water had been added and the mixture had been stirred for 3 hours, 100 ml of 2M sodium hydroxide aqueous solution was added, and the resultant was separated into an aqueous layer and an organic layer. The aqueous layer was extracted with dichloromethane, and the extract was combined with the separated organic layer, dried over anhydrous sodium sulfate, and then concentrated under reduced pressure. The residue was purified with column chromatography (silica gel/hexane:ethyl acetate of 4:1 to 1:1) and then concentrated to afford 3.41 g of (R)—N-(3-(3-trifluoromethylphenyl)propyl)-1-(1-naphthyl)ethylamine as an oil. The compound was dissolved in 10 ml of dichloromethane, 5 ml of 4M hydrochloric acid/dioxane and 20 ml of toluene were added, and the mixture was concentrated under reduced pressure to pureness. The residue was recrystallized from 40 ml of ethanol and 200 ml of heptane to afford 1.71 g of the captioned compound.

$^1$H-NMR (300 MHz, DMSO-d$^6$) δ 1.69 (3H, d, J=6.6 Hz), 2.00 (2H, quintet, J=7.8 Hz), 2.72 (2H, t, J=7.5 Hz), 2.65-2.85 (1H, br), 2.90-3.05 (1H, br), 5.24-5.38 (1H, br), 7.44-7.67 (7H, m), 7.96-8.04 (3H, m), 8.23-8.28 (1H, pseud d), 9.20-9.40 (1H, br), 9.80-10.00 (1H, br) MS (ESI, m/z) 358 (MH+)

Example 1

Effect of Cinacalcet and γ-Glutamylvaline on Antibody Producing Ability

BALB mice (female) of 6 to 8 weeks old were purchased and fed for 1 week for habituation. A commercially available solid feed was used as a feed and tap water was used as water. In order to evaluate influences of cinacalcet and γ-glutamylvaline on antibody producing activity, a culture system using mouse spleen cells was employed. The spleen was collected from BALB-c mice (n=3). The collected spleen cells were washed and thereafter suspended in an RPMI1640 medium (10% FCS, 50 U/ml penicillin, and 50 μg/ml streptomycin). To cells adjusted to 1×10$^6$ per a 48 well culture plate, cinacalcet or γ-glutamylvaline (dissolved in a sterilized phosphate buffer), or a phosphate buffer as a control was added. And the cells were then stimulated with 5 μg of LPS (lipopolysaccharide, obtained from Sigma). Thereafter, the cells were cultured in a CO$_2$ incubator at 37° C. for 5 days and the amount of IgA antibody in the supernatant was analyzed.

In the same manner, the cells adjusted to 1×10$^6$ per a 48 well culture plate were, in the presence or absence of cinacalcet or γ-glutamylvaline, stimulated with 0.5 μg of ConA (concanavalin A). Thereafter, the cells were cultured in a CO$_2$ incubator at 37° C. for 5 days and the amount of IgG antibody in the supernatant was analyzed.

The amounts of IgA and IgG were measured by the ELISA method. The method for measuring IgG is shown below. 100 μl of rat anti-mouse IgG antibody (Calbiochem, 1 μg/ml in 50 mM sodium carbonate buffer, pH 8.5) solution was added to a 96 well ELISA plate and the plate was incubated at 4° C. overnight to coat each well with the anti-mouse IgG antibody. The plate was washed three times with PBST (phosphate buffered saline, 0.05% Tween 20) and subjected to a blocking treatment with 200 μl of PBS solution containing 2% BSA at 37° C. for 1 hr.

The plate was washed three times with PBST. Thereafter, 100 μl of the culture supernatant (9 fold diluted with PBST containing 1% BSA) was added and allowed to react at 37° C. for 2 hr. The plate was again washed four times with PBST. 100 μl of an alkaline phosphatase-conjugated anti-mouse IgG (rabbit) (BD Biosciences) solution diluted 2000 fold with PBST containing 1% BSA was added and allowed to react at 37° C. for 1 hour. The plate was washed six times and then colored with p-nitrophenyl phosphate. The reaction was terminated with 100 μl/well of 3 M NaOH and the absorbance at 405 nm was measured.

The measurement of IgA was carried out in accordance with the method for IgG except that a rat anti-mouse IgA antibody (BD Biosciences) was used as the immobilized antibody, a biotinylated anti-mouse IgA antibody (rat) (BD Biosciences) was used as the labeled antibody, 3,3',5,5'-tetramethylbenzidine solution (TMB substrate-developing solution, Sigma) was used as the chromogenic substrate, termination of the coloring was carried out using 1 M sulfuric acid, and the absorbance at 450 nm was measured.

A statistical analysis was carried out by Student's t test and a significance level of 5% or less was considered as significant difference.

The results are shown in Table 1 and Table 2. Abilities of cinacalcet and γ-glutamylvaline to promote IgA production upon LPS stimulation were significantly confirmed. Abilities to promote IgG production upon ConA stimulation were also significantly confirmed.

TABLE 1

Effects on the amounts of IgA production upon LPS stimulation of mouse spleen cells (Alteration in IgA concentration (ng/ml))

|  | Control | LPS | LPS + γ-GluVal (0.1 mM) | LPS + Cinacalcet (0.1 μM) |
|---|---|---|---|---|
| Mean | 4.17 | 16.49 | 25.28 | 26.09 |
| Standard deviation | 0.95 | 2.85 | 2.92 | 4.73 |

TABLE 2

Effects on the amounts of IgG production upon ConA stimulation of mouse spleen cells (Alteration in IgG concentration (ng/ml))

|  | Control | ConA | ConA + γ-GluVal (0.1 mM) | ConA + Cinacalcet (0.1 μM) |
|---|---|---|---|---|
| Mean | 7.93 | 41.87 | 62.78 | 55.24 |
| Standard deviation | 0.08 | 6.75 | 6.23 | 3.58 |

Industrial Applicability

The immunostimulating agent of the present invention is able to safely and effectively stimulate immunity. Also, the food or beverage of the present invention has an immunostimulating action.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for stimulating immunity comprising administering an isolated calcium receptor activator to a subject in need of stimulation of immunity, wherein the isolated calcium receptor activator is γ-Glu-Val.

2. A method for treating an infection, diarrhea, polyp, tumor, enteritis or allergy, comprising administering an isolated calcium receptor activator to a patient suffering from infection, diarrhea, polyp, tumor, enteritis or allergy, wherein the isolated calcium receptor activator is γ-Glu-Val.

3. The method according to claim 1, wherein the isolated calcium receptor activator is administered at a dosage of 0.0000001 to 10 g/kg body weight per day.

4. The method according to claim 1, wherein the isolated calcium receptor activator is administered at a dosage of 0.000001 to 1 g/kg body weight per day.

5. The method according to claim 2, wherein the isolated calcium receptor activator is administered at a dosage of 0.0000001 to 10 g/kg body weight per day.

6. The method according to claim 2, wherein the isolated calcium receptor activator is administered at a dosage of 0.000001 to 1 g/kg body weight per day.

* * * * *